United States Patent [19]

Walter

[11] Patent Number: 4,946,681
[45] Date of Patent: Aug. 7, 1990

[54] METHOD TO PREPARE AN IMPROVED STORAGE STABLE NEEM SEED EXTRACT

[75] Inventor: James F. Walter, Ashton, Md.

[73] Assignee: W. R. Grace & Co.-Conn., New York, N.Y.

[21] Appl. No.: 371,353

[22] Filed: Jun. 26, 1989

[51] Int. Cl.$^5$ .............................................. A61K 35/78
[52] U.S. Cl. .................................. 424/195.1; 549/383
[58] Field of Search ....................... 424/195.1; 549/383

[56] References Cited

U.S. PATENT DOCUMENTS 4,556,562  12/1985  Larson .............................. 424/195.1

OTHER PUBLICATIONS

Stokes, et al., *J. Environ. Sci. Health*, A17(1), pp. 57–65 (1982).
Feuerhake, et al., *J. Plant Diseases and Protection*, 89(12), pp. 737–747 (1982).
Schroeder, et al., *J. Natural Products*, 50(2), pp. 241–244 (Mar.–Apr. 1987).
Warthen, Jr., et al., *J. Liquid Chromatography*, 7(3), pp. 591–598 (1984).
Uebel, et al., *J. Liquid Chromatography*, 2(6), pp. 875–882 (1979).
Polasa, et al., *Fd. Chem. Toxic.*, 25(10), pp. 763–766 (1987).
Muthusamy, et al., *Neem Newsletter*, 5(4), Oct.–Dec., p. 48 (1988).
Ladd, Jr., et al., *J. Econ. Entomol.*, 77, pp. 903–905 (1984).
Warthen, Jr., *Sci. Ed. Admin., Agric. Rev. & Manuals., Northeastern Series*, No. 4, Apr. (1979).
Hawley, *Condensed Chemical Dictionary*, Tenth Edition, p. 700 (1981).
Effect of Sunlight on Azadirachtin: Antifeeding Potency, J.B. Stokes and R.E. Redfern.—*J. Environ. Sci. Health*, A17(1), 57–65 (1982).
Simple Methods for the Extraction and Formulation of Neem Seeds and Their Effect on Various Insect Pests [German]—K. Feuerhake and H. Schmutterer—*Journal of Plant Diseases and Protection*, 89(12), 737–747 (1982).
A Simplified Isolation Procedure For Azadirachtin, Daniel R. Schroeder and Koji Nakanishi—*Journal of Natural Products*, Vol. 50, No. 2., 241–144, (Mar.–Apr. 1987).
Estimation of Azadirachtin Content in Neem Extracts and Formulations, J.D. Warthen, Jr., et al.—*Journal of Liquid Chromatography*, 7(3), 591–598 (1984).
Preparative Reversed-Phase Liquid Chromatographic Isolation of Azadirachtin From Neem Kernels, Uebel et al., *Journal of Liquid Chromatography*, 2(6), 875–882 (1979).
Mutagenicity Tests of Cashewnut Shell Liquid, Rice-Bran Oil and Other Vegetable Oils Using the *Salmonella Typhimurium*/Microsome System, K. Polasa and C. Rukmini—*Fd. Chem. Toxic*, Vol 25, No. 10, 763–766 (1987).
Evaluation of Neem Products Against Rust Disease of Groundnut, M. Muthusamy, et al., *Neem Newsletter* 5(4) Oct.-Dec., p. 48 (1988).
Japanese Beetle (Coleoptera: Scarabaeidae): The Effects of Azadirachtin on the Growth and Development of the Immature Forms, T.L. Ladd, Jr. et al.—*J. Econ. Entomol.* 77, 903–905 (1984).
*Azadirachta indica*: A Source of Insect Feeding Inhibitors and Growth Regulators, J.D. Warthen, Jr., *Science and Education Administration, Agricultural Reviews and Manuals, Northeastern Series*, No. 4, April (1979).

*Primary Examiner*—John W. Rollins
*Assistant Examiner*—W. Catchpole
*Attorney, Agent, or Firm*—James P. Barr

[57] ABSTRACT

A process for the production of stable azadirachtin solutions comprising extracting ground neem seeds with a solvent having azadirachtin solubility to produce an aqueous-containing azadirachtin extract solution and then adding an effective amount of 3–4 Angstrom molecular sieves to selectively remove water from the extract to yield a storage-stable azadirachtin solution having less than 5% water by volume.

4 Claims, No Drawings

METHOD TO PREPARE AN IMPROVED STORAGE STABLE NEEM SEED EXTRACT

BACKGROUND OF THE INVENTION

1. Field of the Invention

This invention relates to pesticide compositions, and more specifically to a process for improving the storage stability of neem seed extracts which contain azadirachtin as the active pesticidal ingredient by contacting the extracts with an adsorbent capable of selectively removing water.

2. Description of the Prior Art

The biological activities of the neem tree seeds have long been recognized. Of primary importance are the potent pesticidal properties of azadirachtin, the main active ingredient in the neem seed. Azadirachtin is a tetranortriterpenoid that causes feeding inhibition and growth disruption in various insect, mite, nematode, etc. orders.

There are various methods known in the prior art to extract azadirachtin from neem seeds. Typically, these methods involve drying the neem seeds, milling the dried seeds to a coarse powder, and extracting the powder with various solvents such as methanol, ethanol, water, methylene chloride, chloroform, hexane, methylethylketone, butanol, petroleum benzene, ether, acetone, methyl tertbutyl ether, diethylcarbonate, etc. In general, it has been found that the efficiency of the extract yield can be increased by increasing the solvent polarity, i.e., from hexane to ethanol, ethanol to methanol, methanol to water, etc. However, despite the initial drying of the neem seeds, they still contain between 6 to 15% water. Thus, while the utilization of more polar solvents will increase the extraction efficiency relative to azadirachtin, it will also extract more of the water contained within the neem seeds and results in aqueous-containing extracts. That is, since water and azadirachtin have similar solubilities, the solvents useful for extracting the azadirachtin from neem seeds also extract any water contained therein. Crude neem seed extracts will typically contain up to 20% water. It now has been discovered that the presence this high concentration of water in neem seed extracts is a primary cause of the degradation of azadirachtin in solution.

SUMMARY OF THE INVENTION

An object of this invention is to increase the storage stability of azadirachtin in neem seed extract formulations.

Another object of this invention is to provide a method of selectively removing water from neem seed extracts.

Under the process of this invention, it has been discovered that 3 to 4 Angstrom molecular sieves will selectively remove water from neem seed extracts without removing the active pesticidal compound azadirachtin.

DETAILED DESCRIPTION

The present invention is directed to a process for improving the shelf stability of the active pesticidal compound azadirachtin in neem seed extracts by selectively removing water from the extracts. As used herein, the term "selectively removing water" refers to a process that specifically removes only water and does not remove any azadirachtin from the neem seed extract.

The process for selectively removing water from neem seed extracts comprises selecting a neem seed extract, determining the water content of the extract, contacting the extract with an effective amount of 3 to 4 Angstrom molecular sieves, allowing the water to be absorbed by the molecular sieves, and separating the resulting water depleted neem seed extract from the molecular sieves.

The acceptable concentration of water in the finished neem seed extract can vary greatly depending upon the particular solvent system of the extract. There are two basic solvent systems found to be acceptable for use in storage stable neem seed extracts, namely alcohols and "aprotic" solvents. In accordance with this invention, the storage stability of azadirachtin neem seed extracts is enhanced when the extract solution comprises either: greater than 50% by volume aprotic solvents and less than 15% water, or greater than 50% by volume alcohol and less than 5% water.

Aprotic solvents are defined as polar solvents having moderately high dielectric constants, which do not contain acidic hydrogen, Morrison and Boyd, *Organic Chemistry* 3rd. Edition, 31 (1974). The various factors that determine whether a given solvent is protic or aprotic are only qualitatively understood. The proton donating or proton accepting interaction is usually greatest when the atom attached to the proton is nitrogen or oxygen. This behavior has been attributed to hydrogen bonding. In general, the hydrogen bond strength increases with increasing acidity of the proton-donating group, and increasing basicity of the proton-accepting group. Solvents suitable for use in this invention will be those solvents that do not contain acidic or basic functional groups and those solvents that do not degrade into acids or bases.

The preferred aprotic solvents for use in this invention include, but are not limited to, alcohols, ketones, nitriles, substituted aromatics, chlorinated aliphatics, aromatic aldehydes, sulfones, ethers, esters, and the like, or mixtures thereof. Various other solvents having the above aprotic characteristics are known to those skilled in the art, and the choice of a particular solvent is not per se critical to the invention, provided that azadirachtin has a high degree of solubility therein, and the solvent does not cause degradation of the azadirachtin by proton donating or proton accepting interactions.

Suitable alcohols for use in this invention include but are not limited to, methanol, ethanol, propanol, 2-propanol, butanol, 2-butanol, t-butanol, and the like.

Those solvents known to degrade azadirachtin include bases such as amines or hydroxides, acids such as mineral acids or carboxylic acids, amides, water, and certain aprotic solvents such as DMSO which contain sulfoxides. However, the final formulations of this invention may contain minor amounts of these solvents, typically less than 1% by volume for the control of pH and the like.

The amount of molecular sieves to be added to the neem seed extract can vary widely depending on the initial amount of water contained in the extract. Since the water content of neem seeds varies greatly, typically between 6% to 15% water, the resulting extracts will typically contain between about 10% to about 30% water. The typical water absorption capacity of the 3 to 4 Angstrom molecular sieves is about 0.20 grams water per gram molecular sieve.

One skilled in the art, knowing the initial amount of water in the extract, will readily be able to determine an appropriate amount of molecular sieves to add to the extract in order to achieve the final desired water content of this invention.

In a preferred embodiment, coarsely ground neem seeds are first extracted with a non-polar azadirachtin-insoluble solvent such as hexane to remove neem oil from the seeds. The defatted neem seeds are then extracted with an azadirachtin-soluble solvent to obtain an azadirachtin solution. To this solution is added an effective amount of 3 to 4 Angstrom molecular sieves to selectively remove water from the extract.

The general principle behind this invention, i.e., selectively removing water from azadirachtin extracts, can be applied to any water-containing neem seed extract independent of the particular solvent system used.

Without further elaboration, it is believed that one skilled in the art, using the preceding detailed description can utilize the present invention to its fullest extent.

The following examples are provided to illustrate the invention in accordance with the principles of this invention, but are not to be construed as limiting the invention in any way except as indicated in the appended claims. All parts and percentages are by weight unless otherwise indicated.

EXAMPLE 1

To produce the improved formulation in this process, neem seeds were first ground in a mill to 5 mesh. The neem seeds were then extracted with hexane to remove the neem oils. Two kgs of ground neem seeds were added to 10 liters of hexane and agitated "mildly" for 24 hours. After the hexane extraction, the seeds were separated from the hexane by filtration or centrifugation. The oilless seeds were then extracted with 95% ethanol to remove the azadirachtin from the seeds. In the ethanol extraction, 0.5 kg seeds were added to 1 liter of 95% ethanol, heated to 70° C., and agitated for 4 hours. The extracted seeds were then filtered from solution and a second 0.5 kg of seeds is contacted with the remaining ethanol. This process is repeated a third time. The final extract had a composition of 4.5 g/l azadirachtin and 16.5% $H_2O$.

EXAMPLE 2

The ethanolic extract from Example 1 was separated into five 100 g samples. To each sample, 10 g of water absorbent were added. The samples were mixed and allowed to sit for 12 hours and then assayed for the presence of azadirachtin (AZAD) and $H_2O$. The results are presented in Table I.

TABLE I

| Sample | % $H_2O$ | AZAD g/l | % $H_2O$ Removed | % AZAD Retained |
|---|---|---|---|---|
| Initial Sample | 16.5 | 4.5 | — | — |
| Alumina | 16.4 | 4.5 | 0.6 | 100 |
| Anhydrous Potassium Carbonate | 10.3 | 1.5 | 38 | 33 |
| Silica Gel | 16.2 | 4.5 | 1.5 | 100 |
| 3 Angstrom Mole Sieve | 14.7 | 4.7 | 13.3 | 104 |
| Anhydrous Calcium Sulfate | 12.8 | 2.0 | 22.4 | 44 |

Only the 3 Angstrom mole sieves remove $H_2O$ without reducing the azadirachtin content of the solution.

EXAMPLE 3

A portion of the material from Example 1 was split into 4-100 mls samples. To these, 3 Angstrom mole sieves were added at the rate of 20, 30, 40, 80 g of sieves per sample. The samples were sealed and analyzed after agitating 12 hours at room temperature. The results are presented in Table II.

TABLE II

| Sample | Amount of Sieve Added grams | Final $H_2O$ Content % | AZAD g/l | Capacity g $H_2O$/g mole sieve |
|---|---|---|---|---|
| A | 0 | 16.5 | 4.5 | |
| B | 20 | 12.6 | 4.8 | 0.19 |
| C | 30 | 10.8 | 4.9 | 0.21 |
| D | 40 | 8.1 | 4.7 | 0.20 |
| E | 80 | 1.1 | 5.1 | 0.193 |

EXAMPLE 4

Samples from Example 3 were then formulated into a usable formulation by blending in Tween-20, neem oil, PABA, and punctilious ethanol. The final content of each formulation was made up to contain 20% Tween-20, 10% neem oil, 1% PABA, and pH of 3.8. The samples were placed in sealed containers, stored at 55° C. in an incubator and periodically assayed for azadirachtin content.

TABLE III

| | | Azadirachtin Content of Formulated Samples | | | | | |
|---|---|---|---|---|---|---|---|
| | | Hours of Storage | | | | | |
| | | 0 | 100 | 268 | 480 | 1008 | 1280 |
| Sample | % $H_2O$ | | | g/l azadirachtin | | | |
| A | 11.0 | 2.9 | 2.3 | 1.6 | 0.99 | .3 | .21 |
| D | 6.0 | 2.9 | 2.6 | 2.0 | 1.4 | .62 | .47 |
| E | 0.8 | 2.8 | 2.7 | 2.5 | 2.1 | 1.3 | 1.0 |

Results show conclusively that low water content formulation is more stable.

What is claimed is:

1. A process for the production of stable azadirachtin solutions comprising extracting ground neem seeds with an alcoho or aprotic solvent in which azadirachtin is soluble to produce an aqueous-containing azadirachtin extract solution and then adding an effective amount of 3-4 Angstrom molecular sieves to selectively remove water from the extract to yield a storage-stable azadirachtin solution having less than 5% water by volume.

2. A process according to claim 1 wherein the storage-stable azadirachtin solution contains less than 2% water.

3. A process according to claim 1 wherein the storage-stable azadirachtin solution contains less than 1% water.

4. A process for the selective removal of water from alcohol neem seed extracts comprising adding an effective amount of 3 to 4 Angstrom molecular sieves to the alcohol neem seed extract to selectively remove water from the extract and produce a storage stable extract having less than 5% water by volume.

* * * * *